US011266536B2

(12) United States Patent
Timothy (10) Patent No.: US 11,266,536 B2
(45) Date of Patent: Mar. 8, 2022

(54) GRADUATED PRESSURE APPLICATOR (71) Applicant: Jacob Timothy, Leeds Yorkshire (GB)

(72) Inventor: Jacob Timothy, Leeds Yorkshire (GB)

(*) Notice: Subject to any disclaimer, the term of this patent is extended or adjusted under 35 U.S.C. 154(b) by 658 days.

(21) Appl. No.: 15/557,277

(22) PCT Filed: Feb. 29, 2016

(86) PCT No.: PCT/GB2016/050516
§ 371 (c)(1),
(2) Date: Sep. 11, 2017

(87) PCT Pub. No.: WO2016/142650
PCT Pub. Date: Sep. 15, 2016

(65) Prior Publication Data
US 2018/0055694 A1 Mar. 1, 2018

(30) Foreign Application Priority Data
Mar. 11, 2015 (GB) .................................... 1504127

(51) Int. Cl.
A61F 13/00 (2006.01)
A61F 13/08 (2006.01)
A61H 1/00 (2006.01)

(52) U.S. Cl.
CPC ........ *A61F 13/00068* (2013.01); *A61F 13/08* (2013.01); *A61H 1/008* (2013.01)

(58) Field of Classification Search
CPC .... A61H 1/008; A61H 1/006; A61H 2209/00; A61H 9/0078; A61F 13/00068; A61F 13/08; A61F 13/10; A61F 13/06; A61F 2013/0028; A61F 13/00021; A61F 13/0216; A61F 2013/00174; A61M 1/0088
(Continued)

(56) References Cited

U.S. PATENT DOCUMENTS

2009/0299239 A1* 12/2009 Meyer .................... A61H 11/00
601/149
2012/0143113 A1* 6/2012 Robinson ................ A61L 31/06
602/43
(Continued)

FOREIGN PATENT DOCUMENTS

GB   1599607 A  * 10/1981  ........... A61H 9/0078
GB   1599607 A    10/1981
(Continued)

OTHER PUBLICATIONS

Notification of the Transmittal of the International Search Report and Written Opinion of the International Searching Authority from corresponding International Application No. PCT/GB2016/050516 dated May 10, 2016.

*Primary Examiner* — Caitlin A Carreiro
(74) *Attorney, Agent, or Firm* — Nutter McClennen & Fish LLP (57) ABSTRACT The present invention relates to a device for applying graduated pressure to an underlying surface. An exemplary device is a graduated compression device or a graduated pressure bandage, that is able to apply graduated pressure to a limb, with higher pressure being applied at one end of the device, e.g. near the ankle in use, and gradually applying less pressure at the other end of the device, e.g. such that the lowest pressure is applied to the end of the stocking closest to the thigh in use.

19 Claims, 4 Drawing Sheets (58) Field of Classification Search
USPC .................. 128/847, 887; 602/52, 53, 75;
604/93.01, 305
See application file for complete search history.

(56) References Cited

U.S. PATENT DOCUMENTS

2013/0245582 A1\* 9/2013 Croizat ............... A61M 1/0088
604/319
2014/0200494 A1 7/2014 Winkler, Sr. et al.

FOREIGN PATENT DOCUMENTS

GB 2461048 A \* 12/2009 ....... A61F 13/00038
GB 2461048 A 12/2009
WO 2011135078 A1 11/2011

\* cited by examiner

GRADUATED PRESSURE APPLICATOR

CROSS-REFERENCE TO RELATED APPLICATIONS

This application is a U.S. National Phase Application under 35 U.S.C. § 371 of International PCT Application Serial No. PCT/GB2016/050516, filed on Feb. 29, 2016, titled "GRADUATED PRESSURE APPLICATOR," which claims priority to United Kingdom Application No. 1504127.0, filed on Mar. 11, 2015. International PCT Application Serial No. PCT/GB2016/050516 is incorporated by reference herein in its entirety.

The present invention relates to a device for applying graduated pressure to an underlying surface. An exemplary device is a graduated compression device or a graduated pressure bandage, that is able to apply graduated pressure to a limb, with higher pressure being applied at one end of the device, e.g. near the ankle in use, and gradually applying less pressure at the other end of the device, e.g. such that the lowest pressure is applied to the end of the stocking closest to the thigh in use.

Veins, such as those in the legs, transport blood back to the heart through a series of valves that open and close, with muscle contraction preventing backward flow of blood. Various issues such as age, weight, venous disease as well as prolonged sitting or standing can cause problems in the transport mechanism resulting in blood pooling in the lower legs, resulting in painful swelling, and in some cases clotting of the stagnated blood.

For patients who have had a blood clot in their leg (deep vein thrombosis, or DVT), graduated compression stockings have been shown to reduce the risk of developing post-thrombotic syndrome and the risk of having another DVT. Post-thrombotic syndrome is a painful condition developed by some patients who have had a blood clot in their leg and is sometimes referred to as chronic venous insufficiency (CVI) or as post-phlebitic syndrome. Graduated compression stockings can also be used to help reduce the swelling for patients who have developed post-thrombotic syndrome or suffering from venous disease.

Pneumatic compression and intermittent pneumatic compression is a therapeutic technique used in medical pneumatic compression devices that include an air pump and inflatable auxiliary sleeves, gloves or boots in a system designed to improve venous circulation in the limbs of patients who suffer edema or the risk of deep vein thrombosis (DVT) or pulmonary embolism (PE).

In use, an inflatable jacket (sleeve, glove or boot) encloses the limb requiring treatment, and pressure lines are connected between the jacket and the air pump. When activated, the pump fills the air chambers of the jacket in order to pressurize the tissues in the limb, thereby forcing fluids, such as blood and lymph, out of the pressurized area. Typically, a short time later, the pressure is reduced, allowing increased blood flow back into the limb. In intermittent devices the pressure can be increases and reduced a number of times.

The primary functional aim of the device is to squeeze blood from the underlying deep veins, which, assuming that the valves are competent, will be displaced proximally. When the inflatable sleeves deflate, the veins will replenish with blood. The intermittent compressions of the sleeves will ensure the movement of venous blood.

Graduated compression stockings are also known and are used to promote circulation in a wearer's legs. Graduated compression stockings apply a certain amount of pressure near the wearer's ankle and then apply gradually less and less pressure as they move up the leg. In this way, they help to squeeze or push blood back up the leg from the ankle to the thigh in an effort to counteract pooling of blood in the leg and the resultant swelling. Graduated compression stockings are typically knitted or woven legwear where the material use is manufactured to provided graduated pressure. The stockings come in various versions such as tube bandages, knee highs, thigh highs, and pantyhose or leggings and are often described with reference to millimeters of mercury (mmHg), which represents the amount of pressure applied in use by the stockings. The gradient pressure is strongest at the ankle and decreases up the leg.

In some instances, graduated compression stockings may be used to help prevent a DVT from occurring in a patient who has never had one. For example, a physician may have a patient wear graduated compression stockings after surgery or when bedridden to help promote circulation. Compression stockings are also marketed and recommended for use on flights, particularly long haul flights, where an increased risk of DVT has been identified. They are also used for general wear by individuals who spend a significant time sitting or standing and suffer from associated leg pain. There have however been problems associated with such stockings as they can place too much pressure in certain areas resulting in further problems.

The present invention aims to obviate or mitigate problems associated with the prior art.

The preceding discussion of the background to the invention is intended only to facilitate an understanding of the present invention. It should be appreciated that the discussion is not an acknowledgement or admission that any of the material referred to was part of the common general knowledge as at the priority date of the application.

Throughout the description and claims of this specification, the words "comprise" and "contain" and variations of the words, for example "comprising" and "comprises", means "including but not limited to", and is not intended to (and does not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers or characteristics, and compounds described in conjunction with a particular aspect, embodiment or example of the invention are to be understood to be applicable to any other aspect, embodiment or example described herein unless incompatible therewith.

According to an aspect of the present invention there is provided a device for applying pressure to an underlying surface, said device comprising a sealed enclosure having at least one compartment; an fluid evacuation valve or aperture for evacuating fluid from the at least one compartment; and a plurality of spaced apart pillar-like structures positioned within the at least one compartment; characterised in that the pillar-like structures are arranged in pillar sets of two or more pillar-like structures, the pillar-like structures in a first pillar set differing in arrangement or physical characteristics such as height or hardness from the pillar like structures in a second pillar set, such that when fluid is evacuated from the at least one compartment the pressure applied to an underlying surface by the first pillar set is different to the pressure applied to an underlying surface by a second pillar set during the same fluid evacuation event.

The device is provided with a plurality of pillar sets, each pillar set comprising at least two neighbouring pillar-like structures. The distance between the at least two pillar like structures reduces when fluid is evacuated. As the device is provided with a plurality of pillar sets, with the physical or material characteristics of the pillar-like structures in a first pillar set being different to those characteristics in a second pillar set, the device is able to apply more pressure in some regions than others i.e. the region of the device associated with or proximate to the first pillar set will apply a different pressure to an underlying surface when air is evacuated than the region of the device associated with or proximate to the second pillar set. This allows the pressure applied to the underlying surface to differ as you travel along an axis.

In a preferred embodiment the pressure applied to an underlying surface is graduated along an axis e.g. along a vertical axis such that more pressure is applied at one end than the other. Alternatively the pressure may vary along an axis such that there is higher pressure applied at both the top and bottom of a bandage with less pressure applied in a central area.

Preferably pillar sets are arranged along an axis, preferably a longitudinal axis, such that the pressure applied to an underlying surface by a pillar set (or region of the device proximate said pillar set) is different at different points along said axis, for example it lessens as you travel along said axis e.g. the pillar like structures in a pillar set at a first end of the device apply the greatest pressure to the underlying surface when fluid is evacuated, and as you travel along the length of the device the pillar sets apply less pressure to the underlying surface during the same fluid evacuation event.

Preferably the first pillar set of pillar-like structures is positioned at a first end of the device, with one or more additional pillar sets of pillar-like structures being positioned towards an opposing second end of the device, such that when air is evacuated from the at least one chamber the device applies graduated pressure along an axis to an underlying surface.

Preferably the device is a medical compression device suitable for improving circulation in a limb (or limbs) of a patient. The device may be akin to an intermittent pneumatic compression device, however rather than pressure being applied when air is fed into the device as with current such devices, with this device the pressure is applied when air is evacuated from the device. It may therefore be considered to be a vacuum compression device or an intermittent vacuum compression device. Preferably the device can be worn on a limb (e.g. leg or arm). The device may take the form of a tube or sock, or of a planar surface, sheet or envelope which can be wrapped around a limb and secured in place. It will be appreciate that the device could be integrated into other clothing elements as required. In yet further embodiments the underlying surface to which pressure may be applied may not be a limb.

Preferably when the device is in the form of a planar surface, sheet or envelope it is provided with means for securing the device to the surface to which pressure is to be applied. The securing means may be in the form of hook and loop fasteners such as Velcro®, ties or other, preferably releasable, securing means.

The pillar-like structures may be formed from any suitable material. Ideally the pillar-like structures are formed from either a rubber based material, a silicon based material or an elastomeric polymer.

Preferably the pillar-like structures are spaced apart from each other in a predetermined arrangement.

By arranging the pillar-like structures in a predetermined arrangement, the way in which pressure can be exerted onto a body member when air is evacuated from the compartment can be controlled. Optionally the a first pillar set comprises pillar-like structures that are positioned closer to each other than the pillar-like structure in a second pillar set.

Optionally the pillar like structures in the first pillar set are of a different height to the pillar like structures in the second pillar set.

Optionally the first pillar set comprises pillar-like structures with a height of 10 mm and the second pillar set comprises pillar-like structures with a height of 5 mm. Preferably there are one or more additional pillar sets between the first pillar set and second pillar set. Preferably at least some of the additional pillar sets comprise pillar-like structures of a height different to both the first and second pillar sets. Most preferably there are a plurality of pillar sets arranged along a longitudinal axis on the device, with each pillar set comprising pillar like structures of a different height, the heights gradually lessening along the axis. Each pillar set will in itself preferably be arranged along a transverse axis that will at least partially encircle the underlying surface to which pressure will be applied in use.

Alternatively the pillar like structures in the first pillar set are of a different hardness to the pillar like structures in the second pillar set.

Optionally the first pillar set comprises pillar-like structures with a shore hardness of 85 and the second pillar set comprises pillar-like structures with a shore hardness of 35. Preferably there are one or more additional pillar sets between the first pillar set and second pillar set. Preferably at least some of the additional pillar sets comprise pillar-like structures of a shore hardness different to both the first and second pillar sets. Most preferably there are a plurality of pillar sets arranged along a longitudinal axis on the device, with each pillar set (or at least some of the pillar sets) comprising pillar like structures of a different hardness, the hardnesses gradually lessening along the axis. Each pillar set will in itself preferably be arranged along a transverse axis that will at least partially encircle the underlying surface to which pressure will be applied in use.

Preferably the pillar-like structures are cylindrical columns, however, the pillar-like structures may be formed of columns having any suitable cross-sectional geometry. For example, the pillar-like structures could be triangular, rectangular, hexagonal etc in cross-section.

Advantageously each pillar-like structure in a pillar set is connected to a neighbouring pillar-like structure in the same pillar set by a connecting member in order to define a lattice-like structure.

Connecting the pillar-like structures to a neighbouring structure removes the need for re-adjusting the positions of the structures relative to each other after use, as is generally required in the prior art dressings mentioned above that incorporate bead structures.

The connecting members may be integrally formed with the pillar-like structures. Alternatively the connecting members may be bonded with the pillar-like structures.

Optionally at least some pillar-like structures in one pillar set are connected to at least some pillar like structures in a different pillar set.

Preferably the sealed enclosure comprises a first and second film layer.

The first and second film layers may be formed of any suitable material. Ideally the first and second film layers are formed from a vacuum formable material such as PVC.

Preferably the first and second film layers are bonded together around their edges to define the sealed enclosure. The pillar-like structures are thus retained between the first and second film layers The first and second film layers may be bonded together by any suitable means, for example the film layers may be heat sealed, ultrasonically welded or glued together.

Preferably the plurality of pillar-like structures are moveably retained between the first and second film layers.

Preferably the plurality of pillar-like structures are retained in position between the first and second film layers by connection to the first and/or second film layer.

The pillar-like structures may be retained in position between the first and second film layers by any suitable means, for example by a heat seal, an ultrasonic weld or glue.

Preferably the plurality of pillar-like structures are integrally formed with at least one of the film layers.

Preferably a portion of the first film layer is adapted to be drawn into the space between the at least two pillar-like structures when air is evacuated from the compartment. As the first film layer is drawn into the space the dimensions of the wound dressing are reduced, causing a reduction in the distance between the at least two pillar-like structures.

Preferably the fluid evacuation valve is an air evacuation valve. Preferably said valve comprises a vacuum release valve.

The fluid evacuation valve for evacuating fluid/air from the at least one compartment may further comprise a non-return valve in order to prevent the regression of fluid/air into the at least one compartment during the evacuation of air from the compartment.

Preferably a suction means is attachable to the fluid evacuation valve. The device may comprise said suction device but more preferably a standard means for supplying suction that is already available in a medical setting such as a hospital could be utilised.

Preferably the device further comprises means for introducing air into the at least one compartment. The means for introducing air into the at least one compartment may be in the form of a hand pump or an inlet valve connectable to a compressor.

In order to provide a better understanding of the present invention, embodiments will be described, by way of example only and with reference to the following figures in which.

Figure 1A:
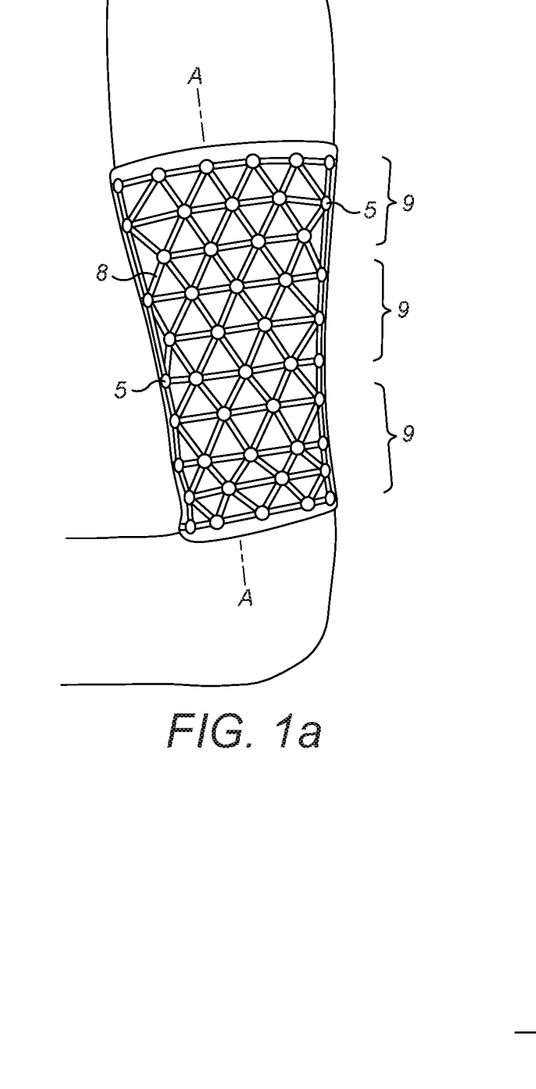
FIG. 1*a* is a general depiction of a graduated compression device according to the present invention.
Figure 1B:
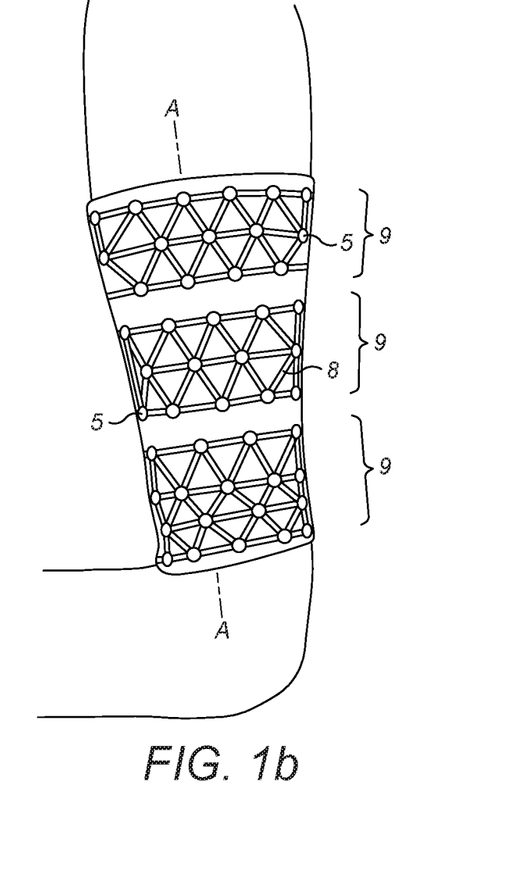
FIG. 1*b* is an alternative embodiment according to the present invention.

A device according to the present invention is generally depicted in FIG. 1 (a and b). This shows a compression device 1 in the form of a tube or sleeve that can be worn by a patient around the leg to apply graduated pressure to the leg. Typically the device is positioned with the with the greatest pressure being applied towards the ankle 2 and the applied pressure reducing as the device extends towards the calf, knee or thigh region. Effectively the ankle region 2 is then more constricted then the higher up the leg.

The depicted devices are translucent but could be transparent or opaque. Translucent or transparent is preferred as it allows the underlying features to be seen.

It will be appreciated that although a tubular device is shown in FIG. 1, the device may be in the form of a sheet or planar bandage which is wrapped around the limb and secured in place by a suitable means such as a band, a strap, VELCRO®, tape or the like. It may also take the form of or be built into pantyhose or leggings etc.

Figure 3:
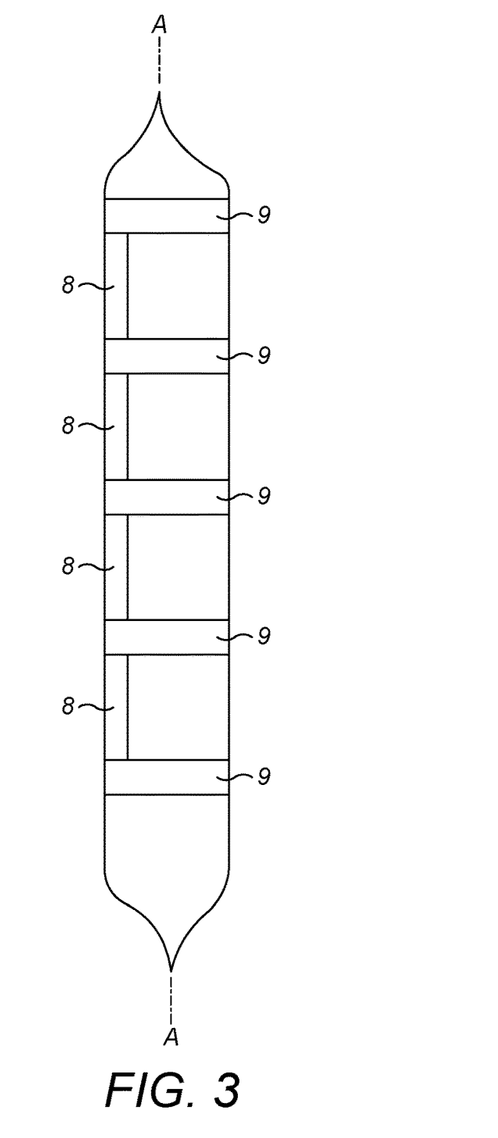
FIG. 3 is a cross-sectional view of a first embodiment of the device of FIG. 1*a* taken along line A-A in FIG. 1*a* showing sets of pillars with different sets exhibiting different hardnesses.
Figure 4:
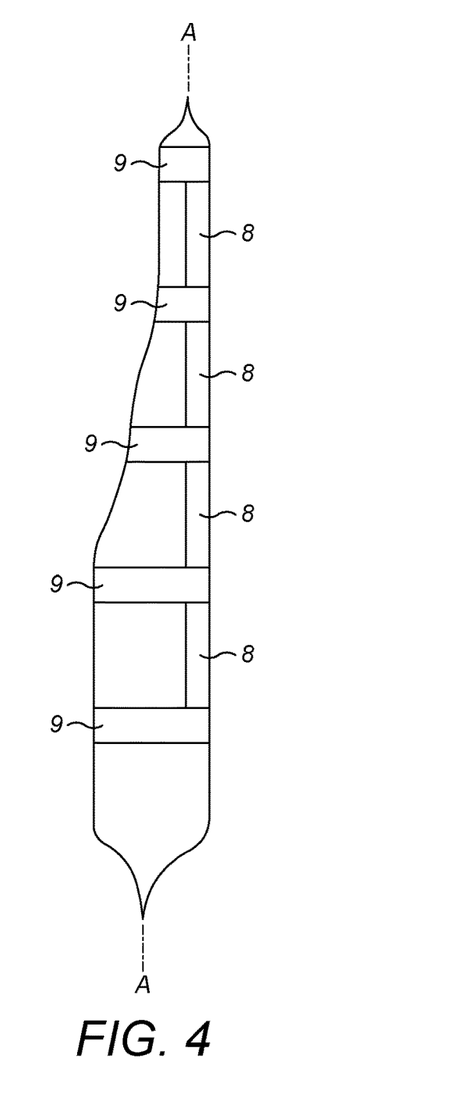
FIG. 4 is a cross-sectional view of a second embodiment of the device of FIG. 1*a* taken along line A-A in FIG. 1*a* showing sets of pillars with different sets comprising pillars of different heights.

As can be best seen in FIGS. 3 and 4, the device comprises a sealed enclosure 3, 30 in the form of a pouch or envelope, having at least one compartment 4, 40 (although it could have multiple compartments); a plurality of spaced apart pillar-like structures 5 (*a, b, c, d* . . . ), 50 (*a, b, c, d* . . . ) positioned within the at least one compartment 4, 40; and means for evacuating air from the at least one compartment (which could be a valve attached to a suction device, not shown).

The sealed enclosure 3, 30 comprises a first film layer 6, 60 and a second film layer 7, 70 which are sealed together around their edges to define the sealed enclosure 3, 30. The first 6, 60 and second 7, 70 film layers may additionally be bonded together at various points in order to define one or more further compartments within the sealed enclosure.

The first 6, 60 and second 7, 70 film layers are made of PVC material and are heat sealed to one another to define the sealed enclosure and/or compartments.

The pillar-like structures 5, 50 (hereinafter referred to as 'pillars') are substantially cylindrical in shape and are connected to a neighbouring structure by means of a connecting member 8, 80. In this arrangement the pillars 5, 50 and the connecting members 8, 80 define a lattice-like structure. Groups of pillars form 'pillar sets' 9.

Figure 2A:
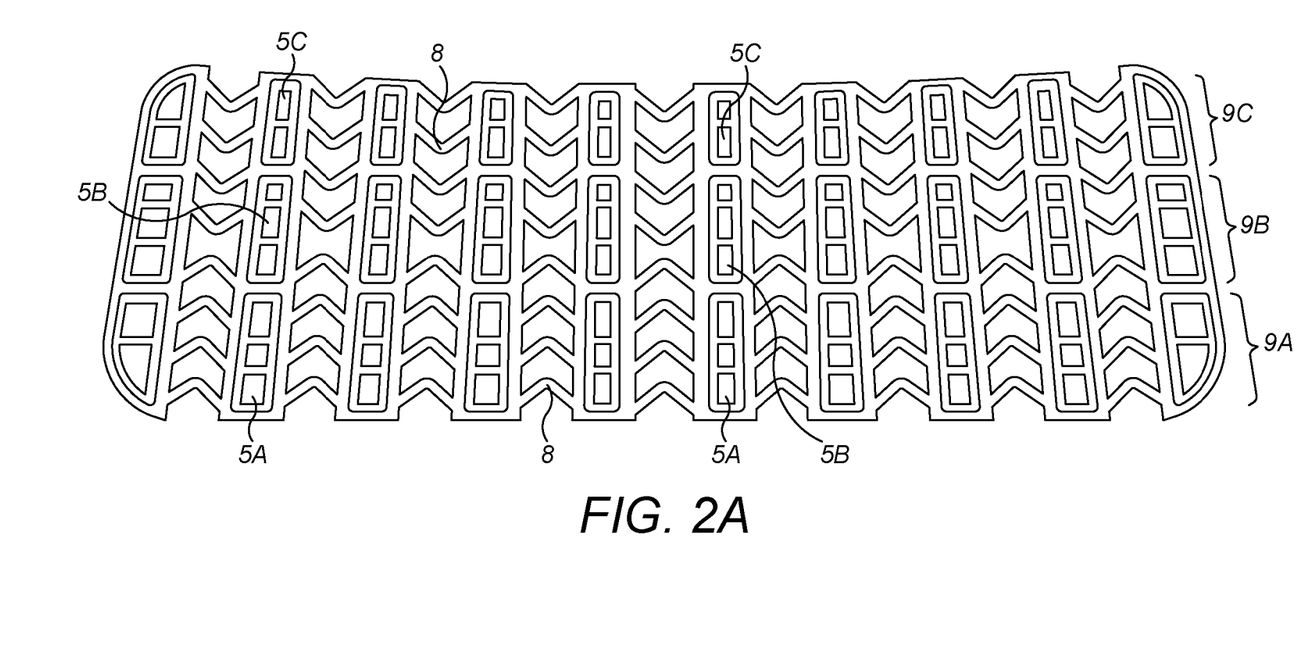
FIG. 2*a* is a depiction of the pillar-like structures and connecting members of the invention.
Figure 2B:
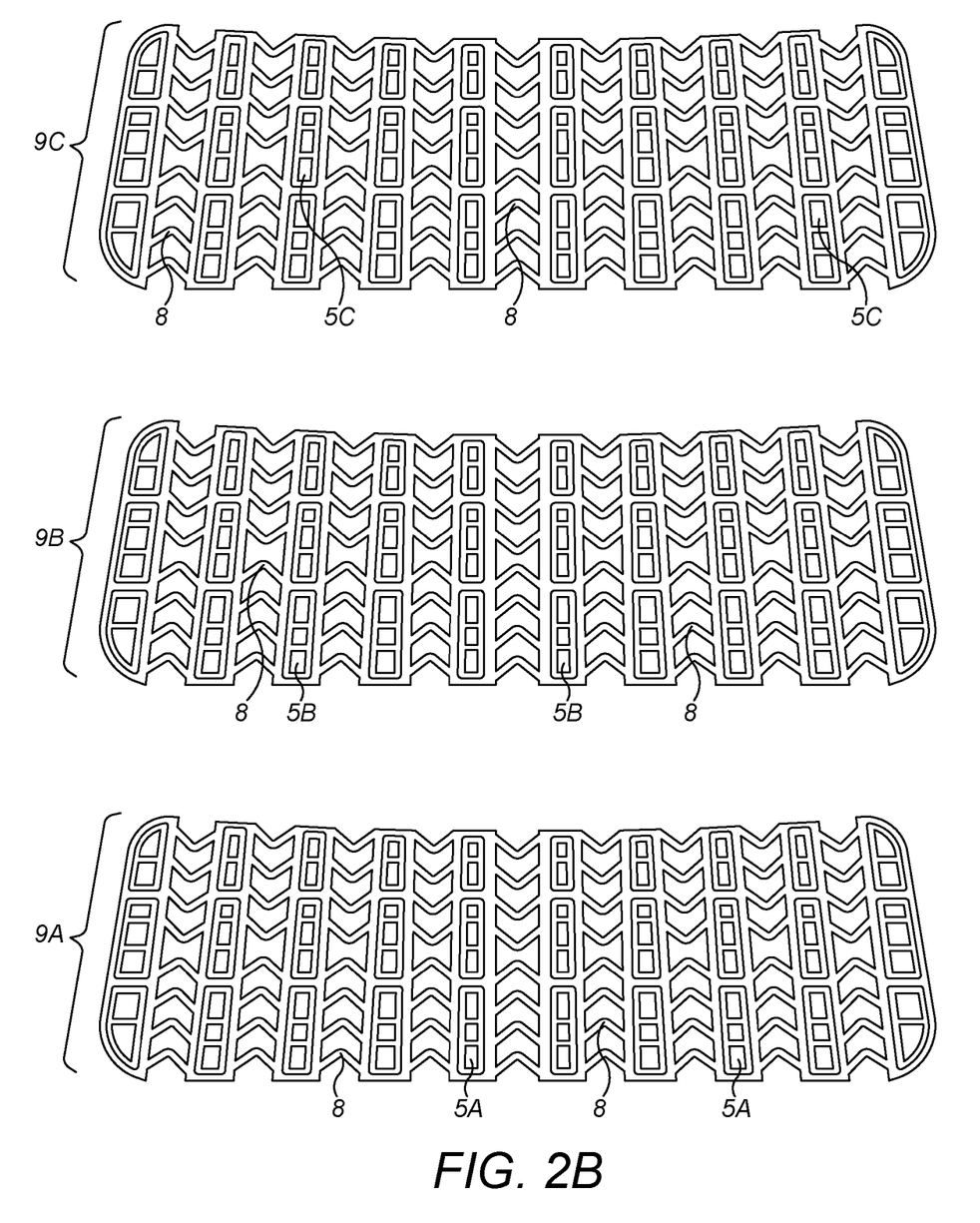
FIG. 2*b* is a depiction of the pillar-like structures and connecting members according to another aspect of the invention

As shown in FIGS. 1*a* and 2*a*, pillar sets 9 (*a, b, c*) can be connected to neighbouring pillar sets 9 by connecting members 8 or, as depicted in FIGS. 2*a* and 2*b* the connecting members 8 may be present only between structures within a pillar set 9 (*a, b, c*).

In a preferred embodiment, the pillars 5, 50 are made from a silicon based material and the connecting members are resilient connecting members and are made of a resilient material such as a flexible plastic material.

The pillars 5, 50 may be moveably retained between the first 6, 60 and second 7, 70 film layers or may be retained in position between the film layers by connection to the first 6, 60 and/or second 7, 70 film layer.

In a particular embodiment, most clearly depicted in FIG. 3, a plurality of pillar sets 9*a*, 9*b*, 9*c* are provided, with each pillar set being made up of groups of pillars 5 (at least two pillars, preferably a strip of pillars positioned to surround or encircle a portion of a limb e.g. like a band or bracelet). Different pillar sets 9 comprise pillars 5 of different hardnesses. A first pillar set 9*a* is provided at one end of the device, the end of the device closest to a user's ankle when worn. A second pillar set 9*b* is provided higher up the device, and a third pillar set 9*c* is provided at the upper region of the device. It will be appreciated that a number of different pillar sets can be used depending on the size of the device and the graduation of pressure required.

The first pillar set 9*a* is formed along a transverse axis which will encircle the ankle portion of a user's leg and the pillars 5*a* are formed of a material with a shore hardness of approximately 85. Further pillar sets 9*b* and 9*c* are provided along the length of the bandage, again encircling the wearers leg, with the shore hardness of the pillars 5b, 5c reducing towards the other end of the bandage, such that at the other end the shore hardness of pillars 5c in the final pillar 9c set is approximately 35. It is preferred that the shore hardness of consecutive pillar sets 9 reduces in a predetermined and graduated manner.

The means for evacuating air from the at least one compartment is in the form of a vacuum release valve (not shown) having a non-return valve in order to prevent regression of air into the at least one compartment during evacuation of air from the compartment.

Pressure is applied onto the limb by evacuating the at least one compartment of air. Evacuation of air results the pulling of the pillars closer together and a reduction of the dimensions of the bandage. When air is evacuated from the compartment, a portion of the first film layer and a portion of the second film layer are pulled into the space between adjoining pillars. As the film layers are pulled into the space by the vacuum left by the evacuation of air therefrom, the surface area of the wound dressing is reduced causing a reduction in the spacing between the adjoining pillars. As different pillar sets comprise pillars of different shore hardnesses this allows the pressure applied by the bandage to be graduated along its length such that the device is able to apply greater pressure at the ankle end than higher up the leg, with pressure showing a graduated change along the longitudinal axis.

As the adjoining pillars are drawn towards one another, the connecting members are caused to flex inwardly into the space.

When air is reintroduced into the compartment the pillars are returned to their original spacing due to the resiliency of the connecting members causing the connecting members to straighten and hence push the pillars away from each other.

The wound dressing further comprises means for introducing air into the at least one compartment (not shown) which may be in the form of a hand pump or an inlet valve connectable to a compressor.

In a further embodiment, depicted in FIG. 4, pillars sets 9 are again provided, with each pillar set being made up of groups of pillars 50 (at least two pillars, preferably a strip of pillars positioned to surround or encircle a portion of a limb e.g. like a band or bracelet). Whilst most features remain the same as the first embodiment, in this embodiment rather than pillar sets of different shore hardnesses, the pillar sets 9a, 9b, 9c comprise pillars of different heights 50a, 50b, 50c.

A first pillar set 9a is provided at one end of the device, the end of the device closest to a user's ankle when worn. The pillar set 9a is formed along a transverse axis which will encircle the ankle portion of a user's leg and the pillars 50a in the set have a height of approximately 10 mm. Further pillar sets 9b, 9c etc., typically of the same material, are provided along the length of the device, again encircling the wearer's leg, with the height of the pillars reducing towards the other end of the bandage such that at the other end the height of pillars 50c in the final pillar set 9c is approximately 5 mm.

Pressure is applied onto the limb by evacuating the at least one compartment of air. Evacuation of air results the pulling of the pillars closer together and a reduction of the dimensions of the bandage. When air is evacuated from the compartment, a portion of the first film layer and a portion of the second film layer are pulled into the space between adjoining pillars. As the film layers are pulled into the space by the vacuum left by the evacuation of air therefrom, the surface area of the wound dressing is reduced causing a reduction in the spacing between the adjoining pillars. As different pillar sets 9 comprise pillars 50 of different heights this allows the pressure applied by the device to be graduated along its length such that the device is able to apply greater pressure at the ankle end than higher up the leg, with pressure showing a graduated change along the longitudinal axis.

As the adjoining pillars are drawn towards one another, the connecting members are caused to flex inwardly into the space.

When air is reintroduced into the compartment the pillars are returned to their original spacing due to the resiliency of the connecting members causing the connecting members to straighten and hence push the pillars away from each other.

The wound dressing further comprises means for introducing air into the at least one compartment (not shown) which may be in the form of a hand pump or an inlet valve connectable to a compressor.

It would be appreciated that the pillars and pillar sets could be arranged to provide graduated pressure along the length of the device by using a combination of different pillar heights and of pillar hardness if required. It would further be appreciated that the number of pillar sets is variable and the embodiments described are merely exemplary in this regard.

It can also be appreciated that, although the embodiments described above relate to a bandage which applied graduated pressure to an underlying surface; an alternative embodiment can apply varying pressure to a surface that is not necessarily simply graduated. For example pressure could be applied to the underlying surface in a manner which varies along a longitudinal axis, for example along the vertical axis in use. In this way there can be portions where less pressure is applied and portions where more pressure is applied. For example there may be pillar sets at the upper and the lower ends of the bandage which allow higher pressure to be applied than the pillar sets in the mid section of the bandage.

When discussing varying pressure in the paragraph above this will be understood to be pressure that is applied by the bandage at a single point in time but which is different at different points along the identified longitudinal axis (rather than simply pressure which varies with time).

It would also be appreciated that the device could provide intermittent pressure by being adapted to evacuate then re-inflate the at least one compartment. This repeated evacuation of air then re-inflation may be automated.

The invention claimed is:

1. A device for applying pressure to an underlying surface, the device comprising: a sealed enclosure having at least one compartment and configured to receive and evacuate fluid; and a plurality of spaced apart pillar-like structures positioned within the at least one compartment, wherein the plurality of pillar-like structures are arranged in pillar sets of two or more pillar-like structures, wherein pillar-like structures in a first pillar set are positioned closer to each other than pillar-like structures in a second pillar set and pillar-like structures in the first pillar set are of a different hardness than pillar-like structures in a second pillar set, such that when fluid is evacuated from the at least one compartment, pressure applied to the underlying surface by the first pillar set is different from pressure applied to the underlying surface by the second pillar set during a single fluid evacuation event.

2. The device according to claim 1, wherein the sealed enclosure comprises a first film layer and a second film layer.

3. The device according to claim 2, wherein the first and second film layers are formed from a vacuum formable material.

4. The device according to claim 2, wherein edges of the first and second film layers are bonded together to define the sealed enclosure.

5. The device according to claim 2, wherein the pillar-like structures are moveably retained between the first and second film layers.

6. The device according to claim 2, wherein the pillar-like structures are integrally formed with at least one of the film layers.

7. The device according to claim 1, wherein each pillar-like structure in a pillar set is connected to a neighbouring pillar-like structure in the same pillar set by a connecting member in order to define a lattice-like structure.

8. The device according to claim 7, wherein the each connecting member is integrally formed with pillar-like structures or is bonded with pillar-like structures.

9. The device according to claim 7, wherein at least some pillar-like structures in one pillar set are connected to at least some pillar-like structures in a different pillar set.

10. The device according to claim 1, wherein the device is a planar surface, sheet or envelope which can be wrapped around a limb and secured in place.

11. The device according to claim 10, further comprising a fastener for securing the device to the underlying surface to which pressure is to be applied.

12. The device according to claim 1, wherein the first pillar set of pillar-like structures is positioned at a first end of the device, with one or more additional pillar sets of pillar-like structures being positioned towards an opposing second end of the device, such that when air is evacuated from the at least one compartment, the device applies pressure along an axis to the underlying surface with different pressures being applied at different points on said axis.

13. The device according to claim 1, wherein the device is a vacuum compression device or an intermittent vacuum compression device.

14. The device according to claim 1, wherein the device is a tube or sock.

15. The device according to claim 1, wherein the pillar-like structures in the first pillar set are of a different height to than the pillar-like structures in the second pillar set.

16. The device according to claim 1, wherein one or more additional pillar sets are positioned between the first pillar set and second pillar set.

17. The device according claim 1, wherein a plurality of pillar sets are arranged along a longitudinal axis on the device, each pillar set of the plurality of pillar sets comprising pillar-like structures of a different height, the heights gradually lessening along the axis.

18. The device according to claim 1, wherein each pillar set is arranged along a transverse axis that will at least partially encircle the underlying surface to which pressure will be applied in use.

19. The device according to claim 1, wherein a plurality of pillar sets are arranged along a longitudinal axis on the device, each pillar set of the plurality of pillar sets comprising pillar-like structures of a different hardness, the hardnesses gradually lessening along the axis.

* * * * *

UNITED STATES PATENT AND TRADEMARK OFFICE
CERTIFICATE OF CORRECTION

| | |
|---|---|
| PATENT NO. | : 11,266,536 B2 |
| APPLICATION NO. | : 15/557277 |
| DATED | : March 8, 2022 |
| INVENTOR(S) | : Jacob Timothy |

It is certified that error appears in the above-identified patent and that said Letters Patent is hereby corrected as shown below:

In the Claims

At Column 8, Claim number 1, Line number 58, please add a --;-- after "set"

At Column 8, Claim number 1, Line number 60, please replace "a" with --the--

At Column 9, Claim number 8, Line number 17, please delete "the" before "each"

At Column 10, Claim number 15, Line number 14, please delete "to" before "than"

Signed and Sealed this
Tenth Day of May, 2022

Katherine Kelly Vidal
*Director of the United States Patent and Trademark Office*